United States Patent [19]

Theodoridis

[11] Patent Number: 4,906,284
[45] Date of Patent: Mar. 6, 1990

[54] HERBICIDAL FLUOROPROPYL COMPOUNDS

[75] Inventor: George Theodoridis, Princeton, N.J.

[73] Assignee: FMC Corporation, Philadelphia, Pa.

[21] Appl. No.: 237,643

[22] Filed: Aug. 23, 1988

Related U.S. Application Data

[63] Continuation of Ser. No. 843,885, Mar. 25, 1986, abandoned, which is a continuation-in-part of Ser. No. 692,794, Jan. 18, 1985, abandoned.

[51] Int. Cl.$^4$ .................. C07D 249/12; A01N 43/653
[52] U.S. Cl. ......................................... 71/92; 548/263; 548/265
[58] Field of Search ..................... 71/92; 548/265, 263, 548/264

[56] References Cited

U.S. PATENT DOCUMENTS

| | | | |
|---|---|---|---|
| 3,922,162 | 11/1975 | Krenzer | 548/263 |
| 4,139,364 | 2/1979 | Wolf | 71/92 |
| 4,213,773 | 7/1980 | Wolf | 71/92 |
| 4,318,731 | 2/1982 | Kajioka et al. | 71/92 |
| 4,398,943 | 8/1983 | Kajioka et al. | 548/263 |
| 4,404,019 | 9/1983 | Uematsu et al. | 548/263 |

FOREIGN PATENT DOCUMENTS

| | | | |
|---|---|---|---|
| 0003619 | 8/1979 | European Pat. Off. | |
| 5632403 | 8/1979 | Japan | |
| 56032468 | 8/1979 | Japan | |
| 5653663 | 10/1979 | Japan | |
| 56-053662 | 5/1981 | Japan | |
| 56-053664 | 5/1981 | Japan | |
| 56-053665 | 5/1981 | Japan | |
| 58-23680 | 2/1983 | Japan | |
| 58-157771 | 9/1983 | Japan | |
| 58-225070 | 12/1983 | Japan | |
| 0136573 | 7/1985 | Japan | 548/265 |
| 60-149571 | 8/1985 | Japan | |
| 60-255780 | 12/1985 | Japan | |
| 783182 | of 1978 | South Africa | |
| 2056971 | 3/1981 | United Kingdom | |
| 2090250 | 7/1982 | United Kingdom | |

*Primary Examiner*—Richard L. Raymond
*Assistant Examiner*—K. Konstas
*Attorney, Agent, or Firm*—Robert M. Kennedy; H. Robinson Ertelt; Abner Sheffer

[57] ABSTRACT

Herbicidal compound of the formula

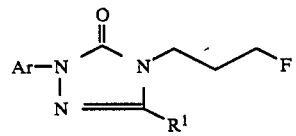

whose Difluoromethyl Analog or Methyl Analog is a herbicide (the Difluoromethyl Analog being identical except that it has a —CHF$_2$ group instead of the —CH$_2$CH$_2$CH$_2$F group of said compound and the Methyl Analog being identical except that it has a —CH$_3$ group instead of the —CH$_2$CH$_2$CH$_2$F group of said compound), Ar being an aryl radical.

3 Claims, No Drawings

HERBICIDAL FLUOROPROPYL COMPOUNDS

This application is a continuation of application Ser. No. 843,885, filed 3/25/86 abandoned, which is a continuation in part of Ser. No. 692,794, filed 1/18/85, now abandoned.

This invention relates to herbicidal 1-aryl-4,5-dihydro-1,2,4-triazol-5(1H)-ones having a fluoropropyl group on the nitrogen at the 4-position of the triazolinone ring.

The herbicidal activity of certain 1-aryl-4,5-dihydro-1,2,4-triazol-5(1H)-ones (otherwise known as 1-aryl-$\Delta^2$-1,2,4-triazolin-5-ones) having a halomethyl or haloethyl group at the 4-position of the heterocyclic ring has been described in the patent literature.

British published patent application 2,090,250 discloses herbicidal compounds of the formula

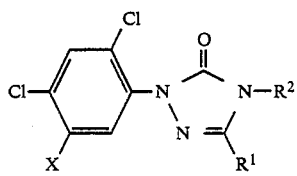

wherein $R^1$ is an alkyl group, $R^2$ is an alkynyl group, a halomethyl group, or a haloethyl group and X is an alkoxy group, an alkenyloxy group, an alkoxyalkoxy group, an alkynyloxy group, a hydroxy group, a halomethyloxy group, or a haloethyloxy group; it indicates that $R^2$ may be trifluoromethyl, difluoromethyl, difluorobromomethyl or difluorochloromethyl.

Japanese Kokai 58-225070 discloses herbicidal compounds of the formula

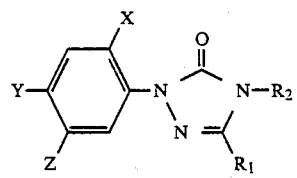

wherein $R_1$ is 1–4C alkyl; $R_2$ is H, 1–4C alkyl, halomethyl or 3–4C alkynyl; X is Cl or F; Y is Cl, Br, OH or $OR_3$; $R_3$ is 1–4C alkyl or benzyl; Z is H, carboxy, cyanomethoxy, $COOR_4$, $COSR_5$ or

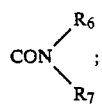

$R_4$ is 1–4C alkyl or 3–4C alkoxyalkyl; $R_5$ is 1–4C alkyl; and $R_6$ and $R_7$ are H, 1–4C alkyl or alkoxy). Examples are listed in which $R_2$ is $CHF_2$.

Japanese Kokai 58-157,771 discloses herbicidal compounds of the formula

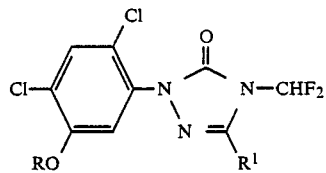

in which $R^1$ is 1–4C alkyl; R is 4–8C alkynyl, 4–8C alkenyl or 3–8C haloalkenyl.

Japanese Kokai 58-023,680 discloses herbicidal compounds of the formula

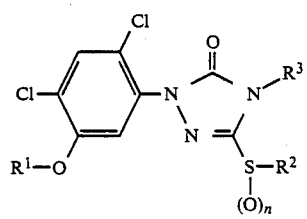

where $R^1$ is lower alkyl or lower alkoxyalkyl; $R^2$ is lower alkyl or benzyl; and $R^3$ is H, 1–6C alkyl, haloalkyl, lower alkoxyalkyl, lower alkynyl or lower alkenyl and n is 0, 1 or 2. Examples are listed with the following haloalkyl radicals at $R^3$: $CHF_2$, $CF_2CH_3$.

Japanese Kokai 60-149571 discloses herbicidal compounds of the formula

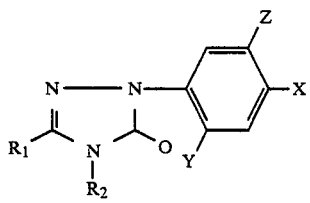

in which
$R_1$ is H or alkyl;
$R_2$ is H, alkyl, alkenyl, alkynyl or haloalkyl;
X and Y are halogen;
Z is nitro, amino or

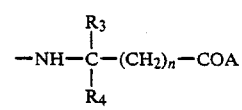

$R_3$ is H or alkyl;
$R_4$ is H or methyl;
n is 0, 1 or 2;
A is $OR_5$, $SR_6$ or $NR_7R_8$;
$R_5$ is H, alkyl, alkenyl or alkynyl;
$R_6$ is alkyl;
Examples are listed in which $R_2$ is $CH_2CF_3$.

Japanese Kokai 60-255780 discloses herbicidal compounds of the formula

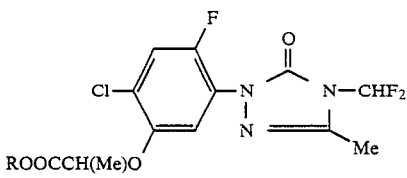

Other patents disclose related compounds in which there is a hydrocarbon substituent at the 4-position of the triazole ring. Thus, U.S. Pat. No. 4,318,731 discloses herbicidal compounds of the formula

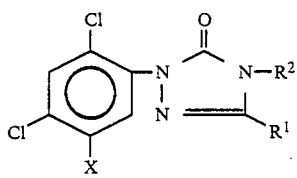

wherein $R^1$ is $C_1$–$C_4$ alkyl; $R^2$ is hydrogen, $C_1$–$C_6$ alkyl or $C_1$–$C_4$ alkenyl; and X is hydroxy, $C_1$–$C_4$ alkyl, $C_1$–$C_6$ alkyloxy, an alkyloxyalkyloxy of which two alkyls may be the same or different and each alkyl is $C_1$–$C_4$, a $C_2$–$C_4$ alkenyloxy, or an alkyloxycarbonylalkyloxy of which two alkyls may be the same or different and each alkyl is $C_1$–$C_4$.

U.S. Pat. No. 4,404,019 discloses herbicidal compounds of the formula

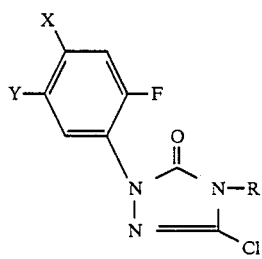

wherein R is a $C_1$–$C_4$ alkyl group, a $C_3$–$C_4$ alkenyl group or a $C_3$–$C_4$ cycloalkyl group, X is a chlorine or bromine atom and Y is a hydrogen atom or a $C_1$–$C_4$ alkoxy group.

Other disclosures of herbicidal 1-aryl-1,2,4-triazolin-5(1H)-ones having a hydrocarbon substituent at the 4-position of the triazole ring are in Japanese Kokais 56-053665, 56-053664, 56-053662, 56-032468 and 56-032403 and U.S. Pat. Nos. 4,139,364 and 4,213,773.

The compounds of this invention are herbicidal aryl-1,2,4-triazolin-5(1H)-ones (such as those in the prior art, e.g. described above) in which, however, there is a fluoropropyl group at the 4-position of the triazole ring. Surprisingly, a compound having the fluoropropyl group has considerably higher herbicidal activity than one having fluoroethyl group at the same position.

The compounds of the invention are those which have the following formula

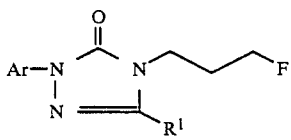

and whose Difluoromethyl Analog or Methyl Analog is a herbicide. The term "Difluoromethyl Analog" is used here to designate a compound which is otherwise identical except that it has a —$CHF_2$ group instead of the —$CH_2CH_2CH_2F$ group of said compound; the term "Methyl Analog" is similarly used here for a compound which is otherwise identical except that it has a —$CH_3$ group instead of the —$CH_2CH_2CH_2F$ group of said compound. Ar is an aryl radical. The aryl radical may be one which is known in the 1-aryl-4,5-dihydro-1,2,4-triazol-5(1H)-one art to give herbicidal compounds when attached at the 1-position of an appropriate 4,5-dihydro-1,2,4-triazol-5(1H)-one. For instance, any of the aryl radicals of the aforementioned disclosures may be used. $R^1$ may be any substituent which does not destroy the herbicidal effect of the Difluoromethyl Analog or the Methyl Analog. Thus $R^1$ may be, for example: H, alkyl of 1–4 carbon atoms, halogen (especially F, Cl or Br), haloalkyl (such as $CH_2F$), lower alkoxy, nitro or —$S(O)_n$—$R^5$ where $R^5$ is lower alkyl or benzyl and n is zero, 1 or 2.

The compounds of this invention preferably have Difluoromethyl Analogs of marked herbicidal properties. For instance the Difluoromethyl Analogs of the preferred compounds show at least 50% kill of at least one of the following species of plants when applied under at least one of the following modes at the rate of 0.5 kg/ha, and more preferably show such kill of at least 50% when applied at the rate of 0.1 kg/ha: Species: velveleaf (*Abutilon theophrasti*), green foxtail (*Setaria viridis*); Modes: pre-emergent, post-emergent. Testing for such herbicidal activity may be carried out in the manner described below (under the heading "Herbicidal Activity").

Ar is preferably a ring-substituted aryl radical. For instance it may have a benzene ring such as the radical indicated by the following formula

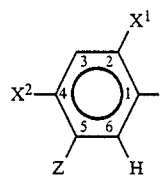

wherein
$X^1$ may be for instance hydrogen or halogen, preferably fluorine or chlorine;
$X^2$ may be, for instance, halogen such as fluorine, chlorine, or bromine, alkyl of 1 to 4 carbon atoms, particularly methyl;
Z may be, for instance, a group —OR. R may be hydrogen, alkyl of 1 to 6 (preferably 1 to 4) carbon atoms (for example, methyl or 1-methylethyl), alkoxyalkyl of 2 to 8 carbon atoms (for example, methoxymethyl), cyanoalkyl of 2 to 5 carbon atoms such as cyanomethyl or 1-cyanoethyl, alkenyl of 2 to 5 carbon atoms such as allyl, alkynyl of 3 to 5 carbon atoms such as propargyl, haloalkynyl of 3 to 5 carbon atoms such as 3-iodopropargyl or 3-bromopropargyl, or a 5- or 6-membered ring heterocyclic group of 1 or 2 same or different heteroatoms selected from O and S (including the S-oxide and S-dioxide) or an alkyl radical of 1 to 5 (preferably 1 to 3) carbon atoms substituted with said heterocyclic group. R may also be a group —$CR^3R^4(CH_2)_n$—CO—$Q^1$—$R^5$ in which n is 0 to 2 (preferably zero); $R^3$ and $R^4$ may be independently hydrogen or alkyl or of 1 to 3 carbon atoms; $Q^1$ may be —O—, —S— or —NR$^7$ and $R^7$ may be H or alkyl of 1–6 (preferably 1 to 4) carbon atoms; $R^5$ may be hydrogen, alkyl of 1 to 6 (preferably 1 to 4) carbon atoms, alkenyl of 3 to 5 carbon atoms such as 2-propenyl, phenyl (which may be optionally ring-substituted) cyanoalkyl of 2 to 6 carbon atoms such as cyanomethyl, alkynyl of 2 to 6 carbon atoms such as propargyl or 1,1-dimethylpropargyl.

As noted above, Z may be —OR where R is heterocyclic. Thus R may be, for instance, 1-methyl-3-pyrrolidinyl, furfuryl or 2-thienylmethyl, or preferably 3-tetrahydrofuranyl, tetrahydrofurfuryl, tetrahydropyran-2-ylmethyl, 1,3-dioxolan-2-yl-methyl, 2-(1,3-dioxolan-2-yl)ethyl, 2,2-dimethyl-1,3-dioxolan-4-ylmethyl, 3-(2-methyl-1,3-dioxolan-2-yl)propyl, 1,3-dioxan-4-ylmethyl, 1,4-benzodioxan-2-ylmethyl, tetrahydro-4H-pyran-4-yl, 5,6-dihydro-2H-pyran-3-ylmethyl, 2,2-dimethyl-1,3-dithiolan-4-ylmethyl, tetrahydro-4H-thiopyran-4-yl, tetrahydrothien-3-yl, 1-oxotetrahydrothien-3-yl, 1,1-dioxotetrahydrothien-3-yl, 2,2-dimethyl-1,1,3,3-tetraoxo-1,3-dithiolan-4-ylmethyl, 1,4-dithiacycloheptan-6-yl, 1,4-dithiacyclohept-5-ene-6-yl, tetrahydro-4H-pyran-3-yl, glycidyl, 2,3-epithiopropyl, 2,2-bis(-chlorodifluoromethyl)-1,3-dioxolan-4-ylmethyl, or 1,1-dioxotetrahydro-4H-thiopyran-4-yl.

Z may also be, for instance, a group —CO—R$^6$ where R$^6$ is hydroxy, alkoxy or alkylthio of 1 to 6 carbon atoms such as methoxy or methylthio, alkoxyalkoxy of 2 to 6 carbon atoms (for example, 2-methoxyethoxy), amino, or alkylamino or dialkylamino wherein each alkyl is of 1 to 6 (preferably 1 to 4) carbon atoms and may be substituted with alkoxy of 1 to 4 carbon atoms (for example, methylamino, dimethylamino, or (methyl)(2-methoxyethyl)amino).

Thus, Z may, for instance, be a group —CO—R$^6$ (such as —CO$_2$H, —CO$_2$alkyl, —CO—S-alkyl, —CO$_2$alkyl-o-alkyl, —CONH$_2$, or —CONH-alkyl or —CON(alkyl)$_2$ in which any alkyl may be substituted with alkoxy), or a group —OR, (including such groups as —OCR$^3$R$^4$CO$_2$R$^5$, —OCR$^3$R$^4$CO—SR$^5$ and —OCR$^3$R$^4$CO—NR$^7$R$^5$).

It will be understood that any alkyl, alkenyl or alkynyl groups of the compound may be straight chain or branched chain. Thus, 1-methylethyl, 2-methylallyl, and 1-methylpropargyl are branched chain examples of alkyl, alkenyl, and alkynyl radicals respectively. The halogen may be fluorine, chlorine, bromine or iodine. The haloalkyl radical may have one or more same or different halogen atoms.

Included in the genus above are compounds in which Z is hydroxy, which, while generally herbicidal at high application rates, are more useful as intermediates than as herbicides. As useful intermediates in the preparation of the more herbicidally active members of the genus, such compounds form a preferred embodiment of the invention.

Compounds in which R is 1-methylethyl or propargyl or halo (e.g. bromo or iodo) propargyl form a preferred embodiment of the invention. The compounds in which Z is —OR and R is the radical —CR$^3$R$^4$(CH$_2$)$_n$—CO—Q$^1$—R$^5$ are also of particular interest, especially where n is O. Usually R$^3$ and R$^4$ will be independently selected from hydrogen and alkyl, and R$^5$ will frequently be alkyl. Preferably R$^4$ is hydrogen and R$^3$ is hydrogen or alkyl such as methyl. Examples of typical such R groups include —CH$_2$CO$_2$C$_2$H$_5$, —CH(CH$_3$)CO$_2$CH$_3$, —C(CH$_3$)$_2$CO$_2$C$_2$H$_5$ and —CH$_2$CONH$_2$.

With respect to the herbicidal trisubstituted-phenyl compounds of this invention, a preferred sub-genus for high herbicidal activity comprises the compounds of the formula

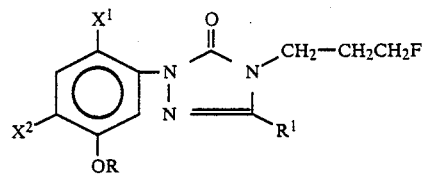

wherein $X^1$ may be either fluorine or chlorine, especially fluorine and $X^2$ may be chlorine or bromine. The substituents R, R$^1$ are also selected as described above. Preferably R$^1$ will be alkyl of 1 to 2 carbon atoms, fluoroalkyl of 1 to 2 carbon atoms, hydrogen, chlorine or fluorine, R may, for instance, be alkyl of 1 to 4 carbon atoms, cyanoalkyl of 2 to 5 carbon atoms, 2-propynyl, 3-halo-2-propynyl, or the radical —CR$^3$H—CO—Q$^1$—R$^5$. Frequently, Q$^1$ will be oxygen and R$^5$ will be alkyl of 1 to 4 carbon atoms. When Q$^1$ is —NR$^7$, R$^5$ and R$^7$ will frequently be selected independently from hydrogen and alkyl of 1 to 4 carbon atoms. The compounds of this sub-genus wherein R is 1-methylethyl or 2-propynyl are among the most active herbicidal compounds of the invention, especially where R$^1$ is methyl and X$^1$ is fluorine.

The present compounds may be prepared by methods described in the literature or by methods analogous or similar thereto and within the skill of the art.

Many of the present compounds may be prepared by treating a compound of the formula

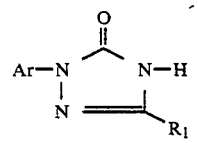

with 1-bromo-3-fluoropropane in the presence of an acceptor of HBr. For instance, a preferred group of compounds may be prepared according to the following reaction sequence.

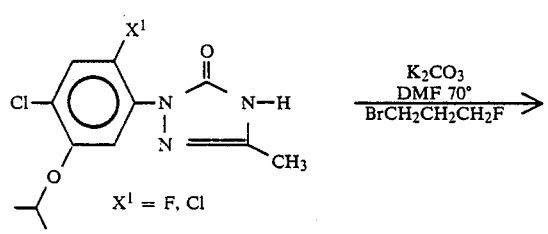

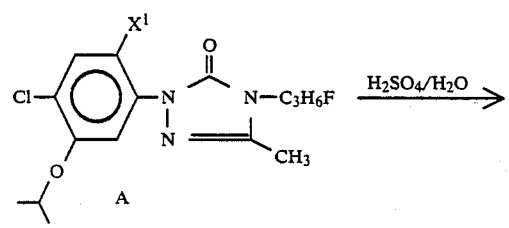

-continued

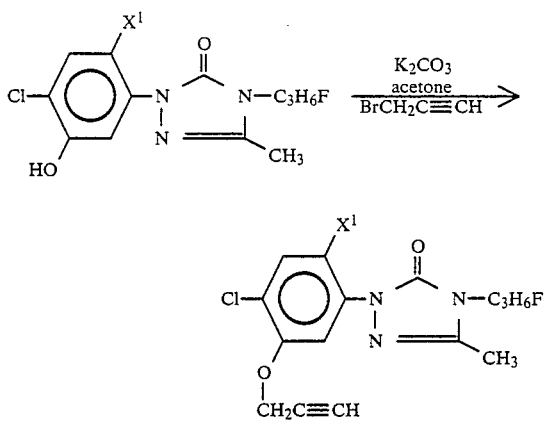

Some representative compounds of this invention are identified in the following table.

TABLE 1

![structure: X1, X2, Z on phenyl ring; N-N=C(R1) triazolinone with N-CH2CH2CH2F]

| Cmpd. No. | X₁ | X₂ | Z | R₁ |
|---|---|---|---|---|
| 1 | F | Cl | OCH(CH₃)₂ | CH₃ |
| 2 | F | Cl | OCH₂C≡CH | CH₃ |
| 3 | Cl | Cl | OCH(CH₃)₂ | CH₃ |
| 4 | Cl | Cl | OCH₂C≡CH | CH₃ |
| 5 | Cl | Cl | OCH₂C≡Cl | CH₃ |
| 6 | F | Cl | OCH₂C≡Cl | CH₃ |
| 7 | F | Cl | OCH₂C≡CBr | CH₃ |
| 8 | F | Cl | OCH(CH₃)C≡CH | CH₃ |
| 9 | F | Cl | OCH(CH₃)CO₂CH(CH₃)₂ | CH₃ |
| 10 | F | Cl | OCH(CH₃)₂ | H |
| 11 | F | Cl | OCH₂C≡CH | H |
| 12 | F | Cl | OCH(CH₃)₂ | Cl |
| 13 | F | Cl | OCH₂C≡CH | Cl |
| 14 | F | Cl | OCH₂C≡CH | F |
| 15 | F | Cl | OCH₂C≡CH | NO₂ |
| 16 | F | Cl | OCH₂C≡CH | SCH₃ |
| 17 | F | Cl | OCH(CH₃)CO₂C₂H₅ | CH₃ |
| 18 | F | Cl | O-CH₂CH₂-O (dioxolane) | CH₃ |
| 19 | F | Cl | OSO₂CH₃ | CH₃ |
| 20 | F | Br | OCH₂C≡CH | CH₃ |

Other representative compounds are those which are identical with compounds 1 and 6–19 respectively except that in each case X₂ is Br. Still other representative compounds are those which are identical with compounds 1 and 6–19 respectively except that in each case X₂ is —OCHF₂. Other representative compounds are those which are identical with compounds 1–20 respectively except that in each case X₁ is Br.

The following Examples illustrate the preparation of the compounds of this invention.

EXAMPLE 1

Synthesis of 1-[4-chloro-2-fluoro-5-(1-methylethoxy)phenyl]-4-(3-fluoropropyl)-4,5-dihydro-3-methyl-1,2,4-triazol-5(1H)-one (Compound 1)

Steps A–E Synthesis of 4-chloro-2-fluoro-5-(1-methylethoxy)aniline from 2-chloro-4-fluorophenol The intermediate 4-chloro-2-fluoro-5-(1-methylethoxy)aniline was prepared in a five-step synthesis from commercially available 2-fluoro-4-chlorophenol as detailed by E. Nagano, et al. in European Patent Application 69,855.

Step F Synthesis of 4-chloro-2-fluoro-5-(1-methylethoxy)phenylhydrazine as an intermediate A stirred solution of 11.0 g (0.054 mole) of 4-chloro-2-fluoro-5-(1-methylethoxy)aniline and 50 mL of concentrated hydrochloric acid was cooled to 0° C. and a solution of 3.7 g (0.054 mole) of sodium nitrite in 15 mL of water was added dropwise. The reaction mixture temperature was not allowed to rise above 6° C. during the addition. Upon completion of addition the reaction mixture stirred at 0° C. for 30 minutes and a solution of 26.8 g (0.12 mole) of stannous chloride in 30 mL of concentrated hydrochloric acid was added dropwise. Upon completion of addition the reaction mixture was stirred at 0° C. for one hour then was filtered to collect a solid precipitate. The solid was slurried in 100 mL of aqueous 25% sodium hydroxide and collected by filtration to give 11.0 g of 4-chloro-2-fluoro-5-(1-methylethoxy)phenylhydrazine.

Step G Synthesis of pyruvic acid, 4-chloro-2-fluoro-5-(1-methylethoxy)phenylhydrazone as an intermediate A stirred solution of 11.0 g (0.051 mole) of 4-chloro-2-fluoro-5-(1-methylethoxy)phenylhydrazine in 50 mL of ethanol and 50 mL of aqueous 1M hydrochloric acid was warmed to 50° C. and a solution of 6.2 g (0.07 mole) of pyruvic acid in 20 mL of water was added. The reaction mixture was filtered to collect 10.0 g of solid pyruvic acid, 4-chloro-2-fluoro-5-(1-methylethoxy)-phenylhydrazone.

Step H Synthesis of 1-[4-chloro-2-fluoro-5-(1-methylethoxy)phenyl]-4,5-dihydro-3-methyl-1,2,4-triazol-5(1H)-one as an intermediate A stirred solution of 10.0 g (0.035 mole) of pyruvic acid, 4-chloro-2-fluoro-5-(1-methylethoxy)phenylhydrazone, 9.6 g (0.035 mole) of diphenylphosphoryl azide and 4.9 mL (0.035 mole) of triethylamine in 200 mL of toluene was heated under reflux for 2.5 hours. The reaction mixture was cooled to ambient temperature and extracted with aqueous 1M sodium hydroxide. The extract was acidified with concentrated hydrochloric acid, which caused an oil to drop out of solution. The mixture was extracted with 100 mL of methylene chloride and the extract concentrated under reduced pressure. The residual oil was slurried with petroleum ether, which caused the oil to solidify. The solid was collected by filtration to give 6.0 g of 1-[4-chloro-2-fluoro-5-(1-methylethoxy)phenyl]-4,5-dihydro-3-methyl-1,2,4-triazol-5(1H)-one; m.p. 120°–124° C.

Step I Synthesis of 1-[4-chloro-2-fluoro-5-(1-methylethoxy)phenyl]-4-(3-fluoropropyl)-4,5-dihydro-3-methyl-1,2,4-triazol-5(1H)-one (Compound 1)

A stirred solution of 1.8 g (0.006 mole) of 1-[4-chloro-2-fluoro-5-(1-methylethoxy)phenyl]-4,5-dihydro-3-methyl-1,2,4-triazol-5(1H)-one, 1.8 g (0.013 mole) of 1-bromo-3-fluoropropane and 0.30 g (0.010 mole) of potassium carbonate in dimethylformamide was heated at 55°–65° C. for 16 hours. The reaction mixture was cooled to ambient temperature and poured into ice-water. The mixture was extracted with diethyl ether and the extract dried with magnesium sulfate. The extract was filtered and the filtrate concentrated under reduced pressure to a residual oil. The oil was subjected to column chromatography on silica gel using 9:1 methylene chloride:heptane as eluant. The appropriate fractions were combined and concentrated under reduced pressure to give 1.0 g of 1-[4-chloro-2-fluoro-5-(1-methylethoxy)phenyl]-4-(3-fluoropropyl)-4,5-dihydro-3-methyl-1,2,4-triazol-5(1H)-one as an oil.

EXAMPLE 2

Synthesis of 1-(4-chloro-2-fluoro-5-propargyloxyphenyl)-4-(3-fluoropropyl)-4,5-dihydro-3-methyl-1,2,4-triazol-5(1H)-one (Compound 2)

Step A Synthesis of 1-(4-chloro-2-fluoro-5-hydroxyphenyl)-4-(3-fluoropropyl)-4,5-dihydro-3-methyl-1,2,4-triazol-5(1H)-one as an intermediate A solution of 0.70 g (0.002 mole) of 1-[4-chloro-2-fluoro-5-(1-methylethoxy)phenyl]-4-(3-fluoropropyl)-4,5-dihydro-3-methyl-1,2,4-triazol-5(1H)-one (prepared in Example 1) in 10 mL of concentrated sulfuric acid was stirred for 30 minutes at ambient temperature. The reaction mixture was poured into ice-water and the mixture was extracted with diethyl ether. The organic layer was dried with magnesium sulfate and filtered. The filtrate was concentrated under reduced pressure to give 0.5 g of 1-(4-chloro-2-fluoro-5-hydroxyphenyl)-4-(3-fluoropropyl)-4,5-dihydro-3-methyl-1,2,4-triazol-5(1H)-one, which was used immediately in the next step of this reaction sequence.

Step B Synthesis of 1-(4-chloro-2-fluoro-5-propargyloxyphenyl)-4-(3-fluoropropyl)-4,5-dihydro-3-methyl-1,2,4-triazol-5(1H)-one (Compound 2)

A stirred solution of 0.5 g (0.002 mole) of 1-(4-chloro-2-fluoro-5-hydroxyphenyl)-4-(3-fluoropropyl)-4,5-dihydro-3-methyl-1,2,4-triazol-5(1H)-one, 0.43 g (0.004 mole) of propargyl bromide and 0.33 g (0.002 mole) of potassium carbonate in 20 mL of acetone was heated under reflux for 5 hours. The reaction mixture was cooled to ambient temperature and filtered. The filtrate was concentrated under reduced pressure to a residual oil. The residual oil was subjected to column chromatography on silica gel using 4:1 methylene chloride:heptane as an eluant. The appropriate fractions were combined and concentrated under reduced pressure to give 0.42 g of 1-(4-chloro-2-fluoro-5-propargyloxyphenyl)-4-(3-fluoropropyl)-4,5-dihydro-3-methyl-1,2,4-triazol-5(1H)-one as an oil.

EXAMPLE 3

Synthesis of 1-[2,4-dichloro-5-(1-methylethoxy)phenyl]-4-(3-fluoropropyl)-4,5-dihydro-3-methyl-1,2,4-triazol-5(1H)-one (Compound 3)

This compound was prepared in the manner of Example 1, Step I, using 3.0 g (0.01 mole) of 1-[2,4-dichloro-5-(1-methylethoxy)phenyl]-4,5-dihydro-3-methyl-1,2,4-triazol-5(1H)-one, 2.8 g (0.020 mole) of 1-bromo-3-fluoropropane and 1.8 g (0.013 mole) of potassium carbonate in 60 mL of dimethylformamide. The yield of 1-[2,4-dichloro-5-(1-methylethoxy)phenyl]-4-(3-fluoropropyl)-4,5-dihydro-3-methyl-1,2,4-triazol-5(1H)-one was 1.6 g as an oil.

Note: The intermediate 1-[2,4-dichloro-5-(1-methylethoxy)phenyl]-4,5-dihydro-3-methyl-1,2,4-triazol-5(1H)-one is a known compound whose synthesis is exemplified in British 2,056,971

EXAMPLE 4

Synthesis of 1-(2,4-dichloro-5-propargyloxyphenyl)-4-(3-fluoropropyl)-4,5-dihydro-3-methyl-1,2,4-triazol-5(1H)-one (Compound 4)

Step A Synthesis of 1-(2,4-dichloro-5-hydroxyphenyl)-4-(3-fluoropropyl)-4,5-dihydro-3-methyl-1,2,4-triazol-5(1H)-one as an intermediate This compound was prepared in the manner of Example 2, Step A, using 1.6 g (0.005 mole) of 1-[2,4-dichloro-5-(1-methylethoxy)phenyl]-4-(3-fluoropropyl)-4,5-dihydro-3-methyl-1,2,4-triazol-5(1H)-one and 35 mL of concentrated sulfuric acid. The yield of 1-(2,4-dichloro-5-hydroxyphenyl)-4-(3-fluoropropyl)-4,5-dihydro-3-methyl-1,2,4-triazol-5(1H)-one was 1.0 g.

Step B Synthesis of 1-(2,4-dichloro-5-propargyloxyphenyl)-4-(3-fluoropropyl)-4,5-dihydro-3-methyl-1,2,4-triazol-5(1H)-one (Compound 4)

This compound was prepared in the manner of Example 2, Step B, using 1.0 g (0.003 mole) of 1-(2,4-dichloro-5-hydroxyphenyl)-4-(3-fluoropropyl)-4,5-dihydro-3-methyl-1,2,4-triazol-5(1H)-one, 1.1 g (0.006 mole) of propargyl bromide and 0.64 g (0.008 mole) of potassium carbonate in acetone. The yield of 1-(2,4-dichloro-5-propargyloxyphenyl)-4-(3-fluoropropyl)-4,5-dihydro-3-methyl-1,2,4-triazol-5(1H)-one was 0.75 g as an oil.

| | NUCLEAR MAGNETIC RESONANCE SPECTRAL ANALYSES |
|---|---|
| Cmpd No. | NMR Data ($\delta$ Values) |
| 1 (CDCl$_3$) | 1.38 (d,6H); 2.10 (m,2H); 2.33 (s,3H); 3.85 (t,2H); 4.58 (t of d, 2H); 4.58 (septet, 1H); 7.23 (d,1H). |
| 2 (CDCl$_3$) | 2.13 (m,2H); 2.33 (s,3H); 2.59 (t,1H); 3.984 (t,2H); 4.51 (t of d, 2H); 4.74 (d,2H); 7.33 (d,1H); 7.36 (d,1H). |
| 3 (CDCl$_3$) | 1.40 (d,6H); 2.10 (m,2H); 2.33 (s,3H); 3.86 (t,2H); 4.57 (t of d, 2H); 4.57 (septet, 1H); 7.06 (s,1H); 7.54 (s,1H). |
| 4 (CDCl$_3$) | 2.12 (m,2H); 2.30 (s,3H); 2.56 (t,1H); 3.83 (t,2H); 4.50 (t of d, 2H); 4.74 (d,2H); 7.11 (s,1H); 7.46 (s,1H). |

HERBICIDAL ACTIVITY

The plant tests species used in demonstrating the herbicidal activity of compounds of this invention include cotton (*Gossypium hirsutum* var. Stoneville), soybean (*Glycine max* var. Williams), field corn (*Zea mays* var. Agway 595S), wheat (*Triticum aestivum* var. Prodax), field bindweed (*Convolvulus arvensis*), morningglory (*Ipomea lacunosa* or *Ipomea hederacea*, velvetleaf (*Abutilon theophrasti*), barnyardgrass (*Echinochloa crus galli*), green foxtail (*Setaria viridis*), johnsongrass (*Sorghum halepense*), yellow nutsedge (*Cyperus esculentus*), and rice (*Oryza sativa*).

Seeds or tubers of the plant test species were planted in furrows in steam sterilized sandy loam soil contained in disposable fiber flats. A topping soil of equal portions of sand and sandy loam soil was placed uniformly on top of each flat to a depth of approximately 0.5 cm.

The flats for the preemergence test were watered, then drenched with the appropriate amount of a solution of the test compound in a mixture of acetone and water containing a small amount (up to 0.5% v/v) of sorbitan monolaurate emulsifier/solubilizer. The concentration of the test compound in solution was varied to give a range of application rates, generally 8.0 kg/ha and submultiples thereof. The flats were placed in a greenhouse and watered regularly at the soil surface for 21 days at which time phytotoxicity data were recorded.

The flats for the postemergence test were placed in a greenhouse and watered for 8–10 days, then the foliage of the emerged test plants was sprayed with a solution of the test compound in acetone-water containing up to 0.5% sorbitan monolaurate. After spraying the foliage was kept dry for 24 hours, then watered regularly for 21 days, and phytotoxicity data recorded.

Phytotoxicity data were taken as percent control. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The present rating system is as follows:

| Rating Percent Control | Description of Main Categories | Crop Description | Weed Description |
|---|---|---|---|
| | | Herbicide Rating System | |
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery | Deficient to moderate weed control |
| 60 | | Lasting crop injury no recovery | Moderate weed control |
| 70 | | Heavy injury and stand loss | Control somewhat less than satisfactory |
| 80 | Severe | Crop nearly destroyed a few survivors | Satisfactory to good weed control |
| 90 | | Only occasional | Very good to |
| 100 | Complete effect | live plants left Complete crop destruction | excellent control Complete weed destruction |

Herbicidal data at selected application rates are given for various compounds of the invention in the tables below. The test compounds are identified in the tables below by numbers which correspond to those used above.

In the Table of herbicidal data below:
"kg/ha" is kilograms per hectare, and
"% C" is percent control.

TABLE 2

Pre-emergence Herbicidal Activity
4-Fluoropropyl Triazolinones

| Compound No. | 1 | 2 | 3 | 4 | 5 |
|---|---|---|---|---|---|
| Rate (Kg/ha) | 0.25 | 0.0625 | 4.0 | 4.0 | 2.0 |
| Species | % C | % C | % C | % C | % C |
| COTTON | 30 | 80 | 100 | 100 | 100 |
| SOYBEAN | 60 | 70 | 100 | 100 | 100 |
| CORN | 100 | 100 | 100 | 100 | 100 |
| RICE | 90 | 80 | 100 | 100 | 100 |
| WHEAT | 100 | 90 | 100 | 100 | 100 |
| FIELD BINDWEED | 60 | 90 | 80 | 100 | 100 |
| MORNINGGLORY | 80 | 100 | 100 | 100 | 70 |
| VELVETLEAF | 100 | 100 | 100 | 100 | 100 |
| BARNYARDGRASS | 100 | 100 | 100 | 100 | 100 |
| GREEN FOXTAIL | 100 | 100 | 100 | 100 | 100 |
| JOHNSONGRASS | 100 | 100 | 100 | 100 | 100 |
| YELLOW NUTSEDGE | 90 | 60 | 100 | 100 | 100 |

TABLE 3

Post-emergence Herbicidal Activity
4-Fluoropropyl Triazolinones

| Compound No. | 1 | 2 | 3 | 4 | 5 |
|---|---|---|---|---|---|
| Rate (K/ha) | 0.25 | 0.0625 | 4.0 | 4.0 | 2.0 |
| Species | % C | % C | % C | % C | % C |
| COTTON | 100 | 90 | 100 | 100 | 100 |
| SOYBEAN | 60 | 70 | 90 | 100 | 90 |
| CORN | 40 | 40 | 100 | 100 | 100 |
| RICE | 20 | 60 | 90 | 100 | 100 |
| WHEAT | 20 | 40 | 100 | 100 | 100 |
| FIELD BINDWEED | 20 | 100 | 100 | 100 | 100 |
| MORNINGGLORY | 70 | 100 | 90 | 100 | 100 |
| VELVETLEAF | 100 | 100 | 100 | 100 | 100 |
| BARNYARDGRASS | 10 | 90 | 100 | 100 | 100 |
| GREEN FOXTAIL | 90 | 100 | 100 | 100 | 100 |
| JOHNSONGRASS | 10 | 80 | 90 | 100 | 100 |
| YELLOW NUTSEDGE | 10 | 50 | 100 | 100 | 90 |

For herbicidal application, the active compounds as above defined are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, water-soluble or water-dispersible granules, as powdery dusts, as wettable powders, as emulsifiable concentrates, as solutions or as any of several other known types of formulations, depending on the desired mode of application.

For preemergence application these herbicidal compositions are usually applied either as sprays, dusts, or granules in the areas in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cotton seed flours, and other organic and inorganic solids which act as dispersants and carriers for the toxicant; these finely divided solids have an average particle size of less than about 50 microns. A typical dust formulation useful herein is one containing 1.0 part of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently, additional wetting agent and/or oil will be added to the tank-mix for postemergence application to facilitate dispersion on the foliage and absorption by the plant.

Other useful formulations for herbicidal applications are emulsifiable concentrates. Emulsifiable concentrates are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Typical wetting, dispersing or emulsifying agents used in agricultural formulations include, for example, the alkyl and alkylaryl sulfonates and sulfates and their sodium salts; polyhydric alcohols; and other types of surface active agents, many of which are available in commerce. The surface active agent, when used, normally comprises 1% to 15% by weight of the herbicidal composition.

Other useful formulations for herbicidal applications include simple solutions of the active ingredient in a dispersant in which it is completely soluble at the desired concentration, such as acetone, alkylated naphthalenes, xylene or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (Alachlor), 2-chloro-N-(2-ethyl-6-methylphenyl)-N-(2-methoxy-(1-methylethyl)acetamide (Metolachlor), and N-chloroacetyl-N-(2,6-diethylphenyl)glycine (Diethatyl-ethyl); benzothiadiazinone herbicides such as 3-(1-methylethyl)-(1H)-2,1,3-benzothiadiazin-4-(3H)-one-2,2-dioxide (Bentazon); triazine herbicides such as 6-chloro-N-ethyl-N-(1-methylethyl)-1,3,5-triazine-2,4-diamine (Atrazine), and 2-{[4-chloro-6-(ethylamino)-1,3,5-triazin-2-yl]amino}-2-methylpropanenitrile (Cyanazine); dinitroaniline herbicides such as 2,6-dinitro-N,N-dipropyl-4-(trifluoromethyl)benzeneamine (Trifluralin); and aryl urea herbicides such as N'-(3,4-dichlorophenyl)-N,N-dimethylurea (Diuron) and N,N-dimethyl-N'-[3-(trifluoromethyl)phenyl]-urea (Fluometuron).

It is apparent that various modifications may be made in the formulation and application of the compounds of this invention, without departing from the inventive concepts herein, as defined in the following claims.

I claim:

1. Herbicidal compound of the formula

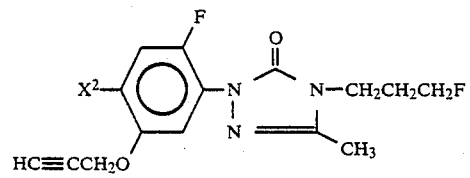

in which $X^2$ is Cl.

2. An herbicidal composition comprising an herbicidally effective amount of the compound of claim 1 in admixture with a suitable carrier.

3. A method for controlling undesired plant growth which comprises applying to the locus where control is desired an herbicidally effective amount of the composition of claim 2.

* * * * *